United States Patent [19]

Pasternack et al.

[11] Patent Number: 4,783,410

[45] Date of Patent: Nov. 8, 1988

[54] CYTOTOXIC T LYMPHOCYTE SERINE ESTERASE AND METHOD FOR STIMULATION AND INHIBITION

[75] Inventors: Mark S. Pasternack, Boston; Herman N. Eisen, Waban, both of Mass.

[73] Assignee: Massachusetts Institute of Technology, Cambridge, Mass.

[21] Appl. No.: 750,323

[22] Filed: Jun. 28, 1985

[51] Int. Cl.[4] ........................ C12N 9/16; C12N 9/48; C12N 9/76
[52] U.S. Cl. .................................. 435/196; 435/212; 435/213
[58] Field of Search ........................ 435/196, 212, 213

[56] References Cited

PUBLICATIONS

Hatcher, V. B., et al. (1978) J. Immunol. 120, 665–670.
"Effects of N"-Tosyl-1-Lysyl-Chloromethylketone on the Activity of Cytotoxic T Lymphocytes[1]", by Tse Wen Chang and Herman N. Eisen, *J. Immunol.*, 124, 1028–1033, (1980).
"The Mechanism of Cell-Mediated Cytotoxicity", by Doug Redelman and Dorothy Hudig, *J. Immunol.* 124, 870–878 (1980).
"Inhibition of Human Natural Cytotoxicity by Macromolecular Antiproteases'", by D. Hudig et al., *J. Immunol.* 126, 1569–1574 (1981).
"Studies on the Mechanism of NK Cell Lysis'", by P-C. Quan et al., *J. Immunol.* 128, 1786–1791 (1982).
"The Requirement for Proteinase Activity for Human Lymphocyte-Mediated Natural Cytotoxicity (NK) Evidence that the Proteinase is Serine Dependent and has Aromatic Amino Acid Specificity of Cleavage[1]", by D. Hudig et al. *J. Immunol* 133 2647–2654 (1984).
"The Site of Action of N-α-Tosyl-1-Lysyl-Chloromethyl-Ketone (TLCK) on Cloned Cytotoxic T. Lymphocytes'", by M. S. Pasternack et al., *J. Immunol.* 131, 2477–2483 (1983).
"Cyclical Changes in Susceptibility of a Myeloma Tumor (LPC-1) /to Immune Destruction", by E. Celis et al. *J. Immunol.* 122, 954–958 (1979).

*Primary Examiner*—Thomas G. Wiseman
*Assistant Examiner*—Charles L. Patterson, Jr.
*Attorney, Agent, or Firm*—Kilpatrick & Cody

[57] ABSTRACT

A novel serine esterase produced by cytotoxic T lymphocytes is insolated and characterized. The protein appears to be membrane bound and has a reduced apparent molecular weight of about 28,000 daltons. Inhibition of the esterase correlates with inhibition of the cells' cytolytic activity. The serine esterase is useful in making antibody and as a target for the inhibition of cytolytic activity by T-lymphocytes, both in vivo and in vitro.

4 Claims, 1 Drawing Sheet

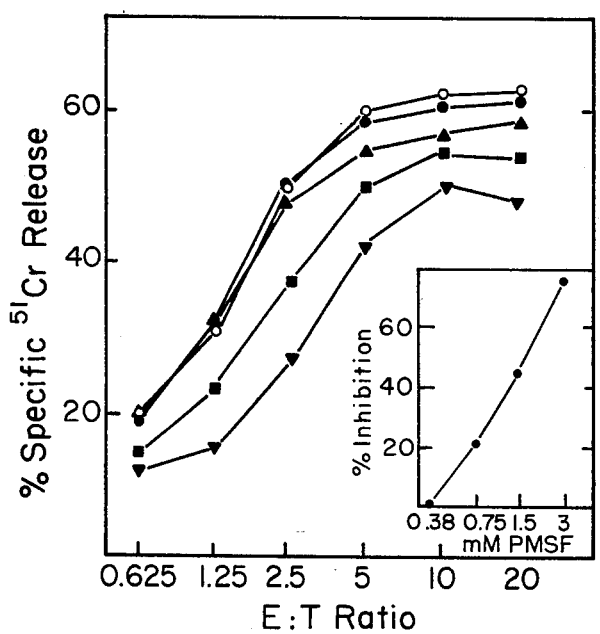

CYTOTOXIC T LYMPHOCYTE SERINE ESTERASE AND METHOD FOR STIMULATION AND INHIBITION

BACKGROUND OF THE INVENTION

The U S. Government has rights in this invention by virtue of National Cancer Institute Grant No. CA-15472; CA-28900; and CA-14051.

This invention relates generally to the field of purified proteins and in particular to a purified serine esterase of cytotoxic T lymphocyte origin.

The vertebrate immune system is characterized by its ability to respond to an enormously diverse set of antigenic determinants. This capability is due to the synthesis by the body of a set of glycoproteins whose specificity for a single antigen is determined by a variable sequence of amino acids which binds to the antigen. The antigen-recognizing glycoproteins produced by B cells are called immunoglobulins. T cells or thymus derived lymphocytes are also capable of recognizing a wide range of different antigens. As in B cells, the ability to recognize a given antigen is also fixed in any particular clonal line. T cells, however, characteristically recognize only antigens located on the surfaces of cells in the specific molecular context of self major histocompatibility complex (MHC) gene products, not as freely circulating antigens. These cells provide a number of different mechanisms for defending the host against invasion by foreign substances and aid in limiting the frequency of tumors (neoplasms).

Unfortunately, these defense mechanisms can create problems, both when they are directed against their own host and when it becomes desirable to maintain foreign cells within the host, as in organ transplantation. Present immunosuppressive therapy following organ transplantation is based on corticosteroids and azathioprine. In addition to their numerous non-immunologic side effects, these agents produce nonselective immunosuppression. As a result, life threatening infections, often due to pathogens of ordinarily low virulence ("opportunistic infections"), are a major problem in the management of allograft recipients. These probems are discussed by R. H. Rubin in "Infection in the renal transplant patient", *Approach to Infection in the Compromised Host,* R. H. Rubin and L. S. Young, eds., pp. 553–605 (New York, Plenum Medical Book Company, 1981). Cyclosporin, a recently introduced immunosuppressive agent, has been associated with direct nephrotoxicity and an increased rate of lymphoid neoplasms.

The pathologic changes present in most human renal allografts reveal infiltration of the allograft parenchyma by a lymphocytic and mononuclear cell infiltrate. Recent observations from both human biopsy material by B. P. Croker, M. J. Borowitz, reported in *Am. J. Clin. Path.,* 78: 707–711 (1982) and W. W. Hancock, N. M. Thomson, R. C. Atkins reported in *Transplantation,* 35; 458–463 (1983) and experimental transplantation in rats by R. Renkonen, A. Soots, E. von Willebrand, and P. Hayry reported in *Cellular Immunology,* 77: 187–195 (1983) show that many of the lymphocytes infiltrating the rejected renal allograft bear the cytotoxic T cell phenotype. Earlier functional studies in vitro by N. L. Tilney, M. R. Garovoy, G. J. Busch, T. B. Strom, M. J. Graves, C. B. Carpenter have demonstrated that these cels are cytotoxic T lymphocytes.

When thymus-derived cells are stimulated by various agents, they differentiate into helper, suppressor, or cytotoxic T lymphocytes. Cytotoxic T lymphocytes (CTL) recognize and lyse target cells and are also thought to serve as an important source of defense against viral infections and possibly against neoplasms. A. E. Lukacher, V. L. Braciale, and T. J. Braciale in *J. Exp. Med.,* 160, 814–824 (1984) and H. D. Engers, A. L. Glasebrook, and G. D. Sorenson in *J. Exp. Med.,* 156, 1280–1285 (1982), review theories and supporting evidence.

The nature of the receptors responsible for antigen-recognition by these cells is rapidly becoming clarified, but the molecular mechanisms responsible for their cytolytic activity remain largely unknown. The possibility that proteases may be involved in this process has been suggested due to the effects of certain inhibitors. T-W Chang and H. N. Eisen, in *J. Immunol.,* 124, 1028–1033 (1980) and D. Redelman and D. Hudig in *J. Immunol.,* 124, 870–878 (1980) demonstrated that the lytic activity of cytotoxic T lymphocytes (CTL) is reduced by exposure to certain protease inhibitors. Similar results have been shown for natural killer cells by D. Hudig, T. Haverty, C. Fulcher, D. Redelman, and J. Mendelsohn, in *J. Immunol.,* 126, 1569–1574 (1981); P-C. Quan, T. Ishizaka, and B. R. Bloom in *J. Immunol.,* 128, 1786–1791 (1982); and D. Hudig, D. Redelman, and L. Minning in *J. Immunol.,* 133, 2647–2654 (1984).

It is therefore an object of the present invention to isolate and characterize a protease, which is produced predominantly by cytotoxic T lymphocytes.

Another object is to produce antibody to the protease produced by the cytotoxic T lymphocytes.

Another object is to produce a gene for polypeptide components of the protease produced by the cytotoxic T lymphocytes.

Yet another object of the present invention is to provide a means for inhibition of the cytolytic activity of the cytotoxic T lymphocytes.

A further object of the present invention is to provide a mechanism for preventing allograft rejection.

SUMMARY OF THE INVENTION

The present invention is a purified 28,000 dalton (apparent molecular weight) protein with serine esterase activity which is produced by lymphocytes, primarily cytotoxic T lymphocytes (CTL) and, in much smaller quantities, thymus cells stimulated to generate CTL.

The 28,000 dalton apparent molecular weight, membrane-bound protease, originally isolated from clones of murine CTL, possesses considerable trypsin-like esterase activity. This activity is blocked completely by two serine esterase inhibitors, diisopropylfluorophosphoridate (DFP) and phenylmethylsulfonyl fluoride (PMSF), but not by $N^{alpha}$-tosyl lysyl chloromethyl ketone (TLCK) at a concentration exceeding that required for complete inhibition of cytotoxicity.

In contrast to the CTL, a wide variety of other lymphocytes, including thymus, spleen, and lymph node cells, established lines of B cells and non-cytotoxic T cells, and clones of T helper cells, all have about 300-fold less esterase activity and far smaller amounts of the protein. However, in thymocytes, the esterase activity increases 20–50 fold and the protein becomes more prominent four days after stimulation in vitro using Con A to generate CTL.

Conventional polyclonal and monoclonal antibodies are produced against the CTL serine esterase using standard immunization techniques.

The gene for the esterase and polypeptide components of the esterase are produced using standard techniques.

In vivo and in vitro immunosuppression is achieved by selective inhibition of the CTL serine esterase. In particular, monoclonal antibodies or agents which inhibit the protein at the active site could he used to decrease or completely stop lytic activity.

BRIEF DESCRIPTION OF THE DRAWING

FIG. 1 is a graph of PMSF inhibition of specific target cell lysis by CTL clone G4.

DETAILED DESCRIPTION OF THE INVENTION

The present invention is a purified 28,000 dalton molecular weight protein with serine esterase activity which is produced by lymphocytes, primarily cytotoxic T lymphocytes (CTL) and, in much smaller quantities, thymus cells stimulated to generate CTL.

In one purification method, extracts of G4 cells, a clone of BALB.B anti H-2D$^d$ CTL described by M. S. Pasternack, M. V. Sitkovsky, and H. N. Eisen in *J. Immunol.*, 131, 2477–2483 (1983), were prepared in phosphate-buffered saline (PBS) containing 0.5% Nonidet-P40 (NP-40). The technique used is as follows.

G4 cells, which are adherent, are harvested by brief exposure to EDTA (5 mM in PBS) after decanting stimulator cell debris. Cells are washed twice in fresh medium, twice in PBS or in RPMI 1640 containing 100 ug/ml bovine serum albumin (5x recyrstallized, Boehringer-Mannheim, Indianapolis, IN), counted, washed a third time in PBS, and then lysed by incubation of 1–2 x $10^7$ cells/ml in PBS containing 0.5% NP-40 (Particle Data Laboratories, Elmhurst, IL) for 20–30 minutes on ice with frequent vortexing.

Trypsin-like esterase activity in the lysate is assayed spectrophotometrically by means of a sensitive coupled reaction involving N$^{alpha}$-benzyloxycarbonyl-L-lysine thiobenzyl ester (BLT), as described by Green and Shaw in *Anal. Biochem*, 93 223–226 (1975). Hydrolysis of BLT yields benzyl mercaptan, which reacts with Ellman's reagent to produce the thiophenoxide chromophore.

Specifically, esterase activity is measured by adding 900 ul of a reaction mixture consisting of 0.2M Tris HCl, pH 8.1; $2 \times 10^{-4}$M BLT [Calbiochem-Behring, San Diego, Calif.]; and $2.2 \times 10^{-4}$M dithiobis [nitrobenzoic acid] [Sigma Chemical Co., St. Louis, Mo.], to 100 ul of appropriate dilutions of cell extracts in NP-40/PBS. After 30 minutes at room temperature, the absorbance at 412 nm is measured in a Gilford spectrophotometer using 100 ul 0.5% NP-40 in PBS plus 900 ul of the reaction mixture as a blank. One unit of esterase activity is defined as an absorbance of 1.0.

The assay results for the following cell extracts or cell extracts plus inhibitors are listed in Table 1. The cell extracts were prepared from: (1) G4, a BALB.B anti H-2D$^d$ CTL clone, described by Pasternack et al. in *J. Immunol.*, 131, 2477–2483 (1983); (2) G4 grown in recombinant human IL-2; (3) B10, a BALB.B anti H-2L$^d$ CTL clone, also described by Pasternack et al. in *J. Immunol.*, 131, 2477–2483 (1983); (4) 1.5.2, a BALB.B anti H-2L$^d$ CTL clone; (5) cr 15, a (B10.BRxB10.D2)F$_1$ anti-BALB minor CTL clone described by Hunig, and Bevan, in *J. Exp. Med.*, 155, 111–125 (1982); (6) O$_3$, a Balb/c T$_h$ clone specific for ovalbumin plus Ia$^d$ described by C. Clayberger et al. in *J. Immunol.*, 133, 1174–1178 1984 ; (7) D$_5$, a (Balb/cxA/J)F$_1$ T$_h$ clone specific for arsanilated protein plus Ia$^d$ described by Rao et al. in *J. Exp. Med.*, 159, 479–494 (1984); (8) A$_6$A$_2$, a T$_h$ hybridoma of B10.A origin fused with BW5147, specific for hen egg lysozyme, provided by Dr. L. Glimcher; (9) EL-4, a T cell leukemia of C57 BL/6 origin; (10) EL-4 maintained in 10% RCASUP; (11) BW5147, T cell lymphoma of AKR origin; (12) BW5147 maintained in 10% RCASUP; (13) BW5147 maintained in 10% RCASUP and 10 ug/ml Con A; (14) P815, mastocytoma of DBA/2 origin; (15) thymocytes harvested from 3 week old BALB/c females; (16) thymocytes cultured for 4 days with 10% RCASUP and 10 ug/ml Con A, described by Irle et al. in *J. Exp. Med.*, 148, 32–45 (1978) ; (17) BALB/c spleen cells following lysis of erythrocytes with NH$_4$Cl; (18) BALB/c spleen cells depleted of T cells by treatment with two anti-Thy 1 monoclonal antibodies and rabbit complement; (19) BALB/c spleen cells cultured for 4 days with *S. Typhosa* lipopolysaccharide (Difco Laboratories, Detroit, Mich.), 10 ug/ml, then depleted of T cells with anti-Thy 1 and complement before assay; (20–22) B cell clones of CBA/N mice described by J. Braun in *J. Immunol.* 130, 2113–2116 (1983).

For the inhibition studies, an aliquot of G4 extract is incubated for 30 minutes at 37° with DMSO or DMSO containing serine esterase inhibitors. Percent inhibition is calculated as (1-[absorbance of treated samples/absorbance of control sample]) x 100; (23) G4 extract pretreated with 2 mM DFP; (24) G4 extract pretreated with 2 mM PMSF; and (25) G4 extract pretreated with $5 \times 10^{-4}$M TLCK.

TABLE 1

| Esterase activity in extracts of cytotoxic T lymphocytes and other cells | |
|---|---|
| Cells | units/$10^6$ cell equivalents |
| *Cytotoxic T Lymphocyte Clones:* | |
| 1. G4 | 172–311 |
| 2. G4 (IL-2) | 203.4 |
| 3. B10 | 67.4 |
| 4. 1.5.2 | 84.3 |
| 5. Cr—15 | 77.6 |
| *Noncytotoxic T Lymphocytes:* | |
| 6. O$_3$ | 0.520 |
| 7. D$_5$ | 0.431 |
| 8. A$_6$A$_2$ | 0.202 |
| 9. EL-4 | 0.572 |
| 10. El-4 (RCASUP) | 0.800 |
| 11. BW5147 | 0.258 |
| 12. BW5247 (RCASUP) | 0.268 |
| 13. BW5147 (RCASUP + Con A) | 0.365 |
| *Other:* | |
| 14. P815 | 0.518 |
| 15. Thymocytes | 0.040 |
| 16. Con A-activated thymocytes | 3.47 |
| 17. Resting spleen cells | 0.557 |
| 18. Splenic B cells | 0.323 |
| 19. Splenic LPS blasts | 0.136 |
| 20. B cell clone 670.6 | 0.259 |
| 21. B cell clone 670.11 | 0.251 |
| 22. B cell clone 750.17 | 0.227 |
| Inhibition Studies | Percent Inhibition |
| 23. G4 (DFP-treated) | 98.7 |
| 24. G4 (PMSF-treated) | 97.2 |
| 25. G4 (TLCK-treated) | 4.6 |

As shown in Table 1, the esterase activity, equivalent to approximately 1 ug of trypsin/$10^6$ cells, was not restricted to G4, since three other CTL clones, B10, 1.5.2, and cr 15, of two different specificities, had roughly comparable activity.

Since all of the CTL clones had been maintained in long-term culture in medium containing 10% rat spleen cell Concanavalin A (Con A) supernatant (RCASUP) and stimulator cells, the stimulator cells and a variety of other cell lines were assayed for esterase activity. The BTL-esterase activities in NP-40 extracts of several different non-cytotoxic cell lines are also summarized in Table 1. The cells used as stimulators to maintain the cultured CTL clones, BALB/c spleen cells and in vitro passaged P815, possess little activity. Two T cell tumor lines, EL-4 and BW5147, also have minimal activity. Furthermore, when these T cell lines are maintained in medium containing 10% RCASUP, or when BW5147 is incubated with both 10% RCASUP and 10 ug/ml Con A, there is no significant increase in enzyme activity. These results establish that the presence of stimulator cells and conditioned medium are not sources of adsorbed esterase activity.

The endogenous character of the esterase activity in CTL is confirmed by two further observations. First, there is no difference between the esterase activity in G4 cells that have been serially cultured twice in recombinant human interleukin-2 (Biogen, Cambridge, Mass.) and in those that are cultured continuously in 10% RCASUP. Second, two T helper cell $T_h$ clones, 03 and D5, that have been maintained in long-term culture with 10% CASUP and intermittently stimulated with antigen-pulsed spleen cells, have negligible activity. A T helper cell hybridoma, A6A2, also has only traces of activity. Thus, among all B and T lymphocytes tested, a high level of esterase activity is expressed only in CTL.

The expression of esterase activity in CTL generated by short-term culture of precursor cells was also measured using the following method. Thymocytes were incubated in culture medium containing RCASUP and Con A, using the method of C. Irle, P-F. Piquet, and P. Vassalli in J. Exp. Med., 148, 32–45 (1978). After four days, viable thymocytes were found to have a level of lectin-dependent cytotoxic activity of 1–4 lytic units ($[LU_{50}]/10^6$ cells measured by the method of J. C. Cerottini, and K. Brunner in Adv. Immunol., 18, 67–132 (1974)). This is comparable to what is seen in conventional mixed lymphocyte cultures. Extracts of these thymocytes have an approximately 50-fold increase in BTL-esterase activity.

As shown in Table 1, the CTL esterase activity is completely inhibitable by the irreversible serine esterase inhibitors DFP and PMSF. It is not, however, inhibited by TLCK, a trypsin inhibitor known to block CTL cytotoxicity and to react with the surface glycoproteins T200 and LFA-1, described by T-W. Chang, and H. N. Eisen in J. Immunol., 124, 1028–1033 (1980); D. Redelman and D. Hudig in J. Immunol., 124, 870–878 (1980); and M. S. Pasternack, M. V. Sitkovsky, and H. N. Eisen in J. Immunol., 131, 2477–2483 (1983).

$^3$H-DFP was used as an affinity-labeling reagent according to the method of L. W. Heck, E. Remond-O'Donnell, and H. G. Remold in Biochem. Biophys. Res. Comm., 83, 1576–1583 (1978) to further characterize the esterase. Although minor $^3$H-labeled components were identified at $M_r=76,000$ and 71,000, the prominent $^3$H-DFP-reactive component was observed at $M_r=28,000$. The higher molecular weight moieties were present at about the same low level in all lymphoid cells tested. However, the level of the 28,000 dalton component clearly varied with the level of the BLT-esterase activity: both were pronounced in extracts of CTL clones but present in only trace amounts in non-cytotoxic cells, and both increased after CTL activity was induced in thymocytes by incubation with Con A.

Further evidence linking the serine esterase activity to the 28,000 dalton protein is provided by their copurification through an affinity chromatography column and an ion-exchange column using the following method.

Greater than $10^9$ adherent G4 cells are harvested by brief exposure to EDTA after decanting stimulator cell debris. The cells are washed twice by centrifugation in complete medium, once in Hanks' balanced salt solution containing 0.1 mg/ml bovine serum albumin, and finally resuspended in phosphate buffered saline (PBS) diluted with 1/10 volume 35 mM $MgCl_2$ and 100 mM HEPES pH 7.4 ("lysis buffer"). The cells are then disrupted at 4° C. with constant stirring by nitrogen cavitation at 300 lbs/in$^2$ for 15 minutes. The lysate is centrifuged at 2000 rpm for 7 minutes to yield a nuclear pellet and a post nuclear supernatant. The nuclear pellet is extracted twice with additional lysis buffer and the supernates pooled with the post nuclear supernatant. The membrane fraction, which contains greater than 99% of the esterase activity, is sedimented at 100,000 g for 1 hour and resuspended in PBS containing 0.5% NP-40 and 0.02% sodium azide (PNA). The suspension is clarified by low speed centrifugation before chromatography.

The membrane fraction is slowly loaded onto a column of lentil lectin-sepharose (Pharmacia Fine Chemicals, Piscataway, N.J.) containing approximately 10 ml of resin. The column is then washed extensively with PNA and esterase activity eluted by washing the column with PNA containing 0.5M alpha methyl mannoside. The eluate fractions containing esterase activity are pooled and dialyzed against Tris HCl 15 mM pH 8.1 containing 0.02% sodium azide.

The dialyzed material is then loaded onto a column of lysine sepharose containing approximately 5 ml of resin. Following extensive washing with 15 mM Tris-HCl pH 8.1, 1% octyl glucoside, 0.02% sodium azide (TOA), esterase activity is eluted by a 60 ml 0–500 mM NaCl gradient in TOA. Esterase activity is monitored in the eluate and the peak fractions pooled. Analysis of the eluted material by SDS-polyacrylamide gel electrophoresis under reducing conditions reveals a protein at greater than 80% purity.

Complete purification is possible using preparative acrylamide gel electrophoresis under nonreducing conditions or gel filtration in the presence of octyl glucoside or by affinity chromatography using monoclonal anti-esterase antibodies coupled to Sepharose as an immunosorbent.

Inhibition of the esterase blocks cytolysis. DFP was not tested because propylene glycol, the solvent in which it is kept, is toxic for cells but PMSF at nontoxic concentrations clearly inhibits lysis of P815 (H-$^2$d) cells by the cloned anti-D$^d$ G4 cells (FIG. 1).

To measure cytolytic activity, the cells are incubated for 30 minutes at 37°, washed, counted, and diluted for titration of cytotoxic activity against $1\times10^4$ $^{51}$Cr-labeled P815 cells. Recovery of G4 is comparable for all the treated samples. In some experiments, DMSO alone is responsible for about 10–15% $^{51}$Cr release from labeled G4 cells but the presence of PMSF at the concentrations shown has no additive toxicity measured either by $^{51}$Cr release or by reduced recovery of viable (trypan blue-negative) G4 cells. CTL assays were performed as described by E. Celis, A. H. Hale, J. H. Russell, and H. N. Eisen in *J. Immunol.*, 122, 954–958 (1979).

The inhibition of cytolytic activity is shown in FIG. 1. The G⁴ cells were suspended in complete medium at about $5\times10^6$/ml and DMSO (control) or PMSF dissolved in DMSO was added to a final DMSO concentration of 3%. ○─○, control with DMSO alone, ·—·, 0.375 mM PMSF; ▲─▲, 0.75 mM PMSF; ■─■, 1.5 mM PMSF, ▼─▼, 3 mM PMSF. The results are expressed as a dose-response curve. One lytic unit ($LU_{50}$) is the number of CTL required for 50% specific lysis of $1\times10^4$ $^{51}$Cr-labeled P815 cells. Percent inhibition = (131 [$LU_{50}$ in presence of PMSF/$LU_{50}$ in absence of PMSF])$\times 100$.

Antibodies specific for CTL esterase may be prepared against the 80% or purer serine esterase. One method for making antibody is as follows: 100–200 ug of protein eluted from the lysine sepharose column is concentrated by ultrafiltration, emulsified with complete Freund's adjuvant, and administered intradermally to each of two rabbits. The injections are repeated with the esterase in incomplete Freund's adjuvant at monthly intervals. Immune sera is collected one week after each injection and screened with an immunoprecipitation assay using G4 CTL extracts treated with $^3$H-DFP as a source of $^3$H esterase and with a solid phase radioimmunoassay using goat anti-rabbit antibodies as a capture antibody, followed by incubation with test sera and probing with $^{125}$I-labeled esterase.

Rabbit antibodies to the individual polypeptides can also be prepared. The polypeptides are separated using preparative SDS-polyacrylamide gel electrophoresis under reducing conditions. The gels are stained, the appropriate bands cut out, and the crushed acrylamide emulsified with adjuvant for immunization as described above. Immune serum is screened by solid phase radioimmunoassay using separate $^{125}$I-labeled polypeptides as probes.

A method for preparing anti-esterase monoclonal antibodies is as follows: rats are immunized subcutaneously with 50 ug of protein eluted from the lysine sepharose column emulsified with complete Freund's adjuvant. Immunization is repeated at 1 month intervals. After assays of test bleedings reveal evidence of antibodies to the esterase, the rats receive a final booster immunization. Four days later spleen and lymph nodes are removed. B cells recovered from these tissues are fused with a suitable myeloma partner, such as P3X63 Ag8-653, to produce hybridomas. Using standard procedures familiar to those skilled in the art, hybridomas secreting monoclonal antibodies to the esterase can be identified, cloned, expanded and used to produce large amounts of the antibody.

The esterase genes may also be cloned using methods familiar to those skilled in the art. Standard techniques such as those described by T. Maniatis, E. F. Fritsch, and J. Sambrook in *Molecular Cloning: A Laboratory Manual* (Cold Spring Harbor Laboratory, 1982) are used to purify polyadenylated RNA from G4 RNA using oligo dT chromatography, to generate cDNA by reverse transcriptase, to convert the cDNA to double stranded DNA using RNAase H and DNA polymerase, to methylate the ds DNA product, and to attach linker oligonucleotide Eco R1 sites for insertion into a lambda phage.

The genes encoding the esterase are cloned using a lambda phage such as the lambda gt 11 recombinant DNA expression vector described by Young and David in *Proc. Natl. Acad. Sci. USA* 89, 1194–1198 (1983). The cDNA inserts are ligated into the Eco R1 site present in the beta gal Z gene. The resulting lambda gt 11 recombinant DNA library is used to infect a high frequency lyzogenization strain. Host cells are blotted onto a nitrocellulose filter and replica plates made. Lysogens are induced, and the nitrocellulose filters probed with the Ig fraction of the rabbit antisera against both native protein and against individual polypeptide chains and with $^{125}$I protein A. Positive clones are purified, and their inserts isolated by Eco R1 digestion. The inserts are ligated into pBR322 plasmids. The plasmids are used to obtain sufficient quantities of the cloned inserts for restriction mapping and sequence determination by the Maxam-Gilbert method.

The serine esterase which is unique to CTL can be used as a basis for specific immunosuppression, particularly once specific inhibitors to the active site are made. These selective chemical immunomodulating agents may provide a means for avoiding the side effects and complications which are presently unavoidable with the broad spectrum immunosuppressives such as the corticosteroids and cyclosporin.

In addition to uses in purification of the serine esterase, anti-esterase antibodies should be useful in inhibiting cytolytic activity by the CTL's in vivo. Specifically, monoclonal anti-esterase antibodies are injected into a patient to be immunosuppressed according to methods known to those skilled in the art. Such methods are taught by A. B. Cosimi et al. in "Treatment of Acute Renal Allograft Rejection with OKT3 Monoclonal Antibody" in *Transplantation* 32, 535–539 (1981) and "The Use of Monoclonal Antibodies to T Cell Subsets for Immunological Monitoring and Treatment in Recipients of Renal Allografts" in *N. E. J. Med.*, 305, 308–315 (1981). In both of these examples, monoclonal antibodies to surface T-cell antigens were intraveneously infused into human patients to reverse graft rejection.

Although this invention has been described with reference to specific embodiments, it is understood that modifications and variations may occur to those skilled in the art. It is intended that all such modifications and variations be included within the scope of the appended claims.

What is claimed is:

1. A serine esterase produced by cytotoxic T lymphocytes wherein said esterase has an apparent molecular weight of approximately 28,000 daltons as determined by SDS gel electrophoresis under reducing conditions and trypsin-like esterase activity not inhibited by N-α-tosyl lysyl chloromethyl ketone at a concentration inhibiting the cytotoxicity of the cytotoxic T lymphocytes.

2. The serine esterase of claim 1 bound to a second molecule to form a dimer.

3. The serine esterase of claim 1 wherein said esterase is isolated by the process comprising the steps of:
   a harvesting cytolytic T lymphocytes;
   b lysing the harvested cytolytic T lymphocytes;
   c isolating the membrane fraction of the lysed T lymphocytes;
   d chromatographing the membrane fraction on a lentil lectin-sepharose column;
   e eluting the esterase-containing fraction with a solution of alpha methyl mannoside;
   f chromatographing the esterase-containing fraction of step (e) on a lysine sepharose column; and g eluting the esterase-containing fraction with a salt gradient in a Tris-octyl glucoside solution.

4. The serine esterase of claim 1 wherein said esterase is isolated by the process comprising the steps of:

a harvesting cytolytic T lymphocytes;
b lysing the harvested cytolytic T lymphocytes; and
c adsorbing the esterase in the lysate of step (b) onto a monoclonal anti-esterase antibody-bound matrix.

* * * * *

UNITED STATES PATENT AND TRADEMARK OFFICE
CERTIFICATE OF CORRECTION

PATENT NO. : 4,783,410
DATED : November 8, 1988
INVENTOR(S) : Mark S. Pasternack et al.

It is certified that error appears in the above-identified patent and that said Letters Patent is hereby corrected as shown below:

Column 7, line 8 delete "●-" and insert -- ●--● --.

Column 7, line 8 delete "▲-▲" and insert -- ▲-▲ --.

Column 7, line 9 delete "■-■" before ", 1.5 mM PMSF" and insert -- ■-■ --; delete "▼-▼" before ",3mM PMSF" and insert -- ▼-▼ --.

Column 7, line 13 delete "(131 [LU$_{50}$ in presence of PMSF/LU$_{50}$" and insert -- (1 - [LU$_{50}$ in presence of PMSF/LU$_{50}$ --.

Signed and Sealed this

Twenty-first Day of March, 1989

Attest:

DONALD J. QUIGG

Attesting Officer

Commissioner of Patents and Trademarks